US00PP09837P

United States Patent [19]

Roberson

[11] Patent Number: Plant 9,837

[45] Date of Patent: Mar. 25, 1997

[54] LANTANA PLANT 'ROBCOMPLAN'

[76] Inventor: Robert J. Roberson, 31706 E. Pink Hill Rd., Grain Valley, Jackson County, Mo. 64029

[21] Appl. No.: 576,493

[22] Filed: Dec. 21, 1995

[51] Int. Cl.[6] ..... A01H 5/00

[52] U.S. Cl. ..... Plt./54.1

[58] Field of Search ..... Plt./54.1, 68.1

*Primary Examiner*—James R. Feyrer

*Attorney, Agent, or Firm*—Rothwell, Figg, Ernst & Kurz pc

[57] ABSTRACT

A new cultivar of Lantana is provided. The very compact growth habit with short internode spacing and strong tendency to self branching, with a continuous multi-colored bloom display, a reduced tendency to set seed, and dense rich forest green leaves providing a cultivar well suite for mass plantings, low borders, hanging baskets or floral specimens.

2 Drawing Sheets

SUMMARY OF THE INVENTION

This invention relates to a new and distinct *Lantana camara* cultivar which is outstanding because of its very compact growth habit, strong tendency to self branching, dramatic multi-colored, continuous bloom display, dense forest green leaves, and tendency to set seed infrequently; and was primarily selected for these characteristics. This selection was made from a specially designed Lantana hybridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America and are woody ornamentals which are not cold hardy North of USDA horticulture Zone 9. the roughish leaves range from yellow-green to green to blue-green and the two basic growth forms are mounding and trailing (weeping). Bloom color usually includes yellow, white, cream, pink, or orange.

The cultivar of *Lantana camara* 'Robcomplan' may further be described as having a number of distinctive characteristics which are enumerated in the succeeding specific description but broadly stated as comprising a very compact growth habit of only 8"–12" (in height and width) in one season, a strong tendency to self branching, a multi-colored bloom display which transitions from yellow (PMS#109) to a sienna tone (PMS#157) and orange (PMS#172), then to fushia pink (PMS#205), dense forest-green (PMS#343) leaves with blue overtones, and reduced tendency to set seed. The continuous color display begins blooming at 6–7 weeks after cuttings are made, or 4 weeks after potting. Almost no pinching is needed due to this cultivar's tendency to self-branching.

I have chosen to identify this new cultivar as *Lantana camara* 'Robcomplan'. It is possible that other identification will be adopted in the trade, but the name selected will serve for the purposes hereof.

BRIEF DESCRIPTION OF THE DRAWING

The accompanying photographs show as nearly true as it is reasonably possible to make the same, in color illustrations of this character, typical leaves and flowers of the new variety. The photographic drawings illustrate the flower form, the distinctive color transitions of the florets, and the very compact growth habit when compared to the comparison plant.

DETAILED DESCRIPTION

Figure 1:
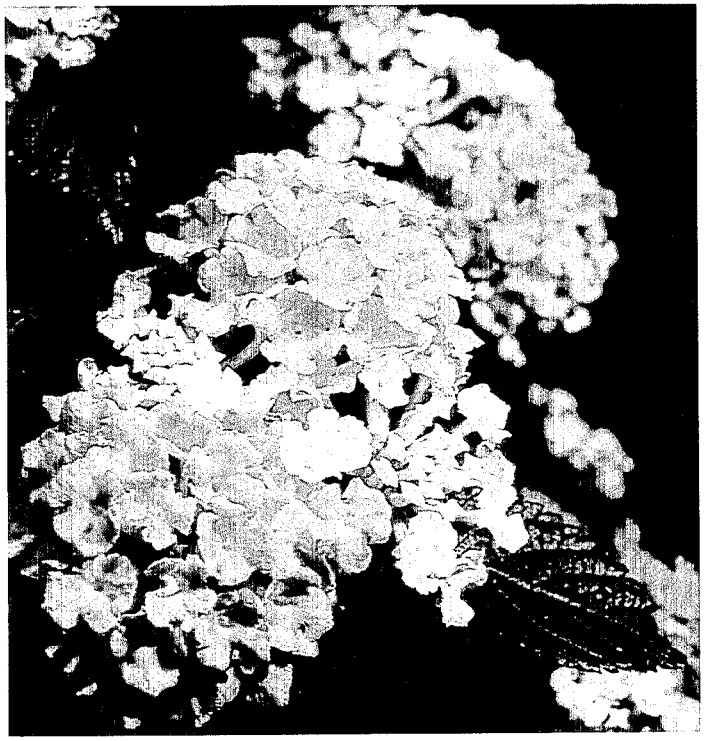
FIG. 1 illustrates the bloom cluster with varying maturity of the florets (to display the color range as well as possible).
Figure 2:
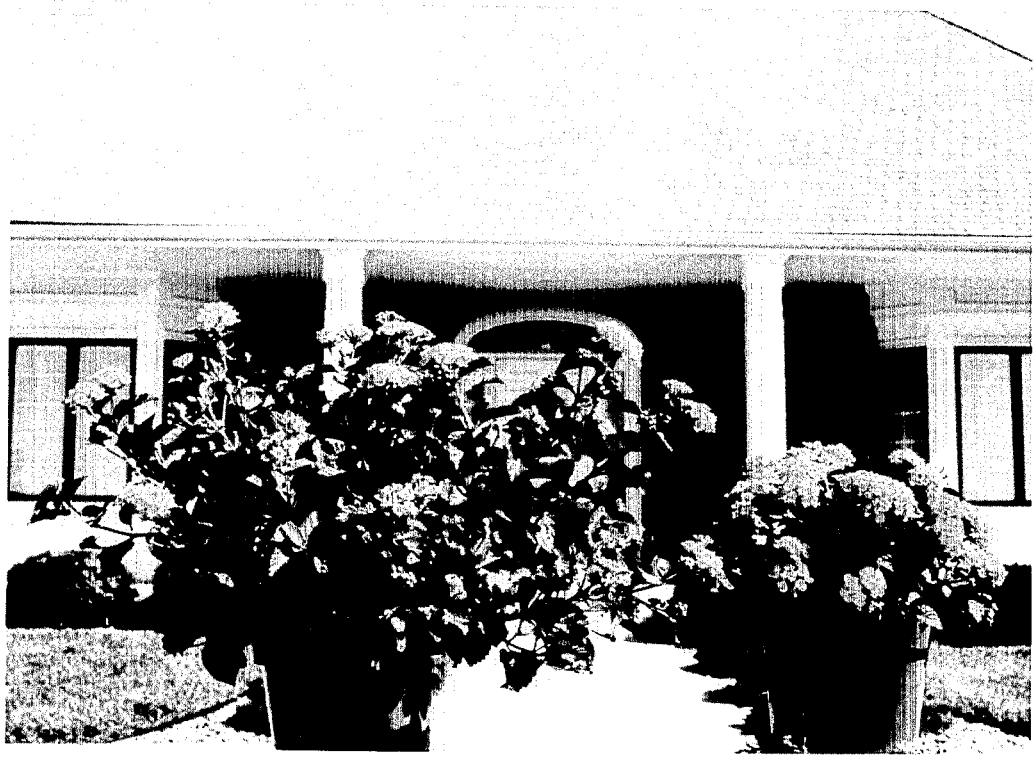
FIG. 2 illustrates the compact growth habit of the mature plant as distinguished from a mature comparison plant.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed parent.*—*Lantana camara* 'Confetti' (in controlled open pollination).

*Pollen parent.*—Unknown.

Propagation: Asexual reproduction by tip cuttings started near Grain Valley, Mo.

PLANT DESCRIPTIONS

Inflorescence and reproductive parts: The inflorescence is a flat topped round cluster of 25–30 florets. The individual clusters are determinate and arise from the leaf axils. Each individual floret is slightly un-symmetrical with a bilateral symmetry and is subtended by a single bract. The perianth consist of: Calyx (5 united petals) and the Corolla (5 united petals with narrow tube). The flowers are zygomorphic, hermaphroditic, and have 4 introse stamens which are didynamous.

The ovary is superior, the style is terminal, and the stigma is lobed. The ovary is 2 locular, but is divided into 4 loculi by a false septum in each loculus. The placentation is axile with 2 ovules per carpel.

The fruit classification is drupe and potentially contains 2 seeds. When fruit forms, it is green (PMS#363); then matures through a deep purple (PMS#533) to a near black (PMS#532)

Inflorescence dimensions:

*Bloom cluster.*—1½" in diameter.

*Single floret.*—¼".

*Pedicle length.*—1.1".

*Corolla tube.*—⅜".

Inflorescence colors:

*Buds.*—Salmon-pink(PMS#163).

*First opening.*—bright yellow (PMS#109).

*Transitions through.*—Sienna (PMS#157) and Orange (PMS#172).

*Maturity.*—Fushia pink (PMS#205).

*Tube.*—Pink in all stages (PMS#212).

Developmental pattern: First flowers develop in a circular pattern on the periphery of the inflorescence.

*Leaves and stems.*—Leaf shape: Ovate. Leaf margins: Serrate. Leaf tip and Base: Acute. Leaf veins: Pinnate. Leaf surface: Rough due to bristly hairs. Leaf arrangement: Opposite. Leaf color: Immature leaves are Forest Green (PMS#349) and mature leaves are Blue Green (PMS#343). Leaf size: Length 2". Petiole: ½". Width: 1¼". Stem: Square in youth becoming round and woody with age.

*Roots.*—highly branched and fibrous

*Flowering time.*—The color display begins blooming at 6–7 weeks after cuttings are made, or 4 weeks after potting, and continue until temperatures drop below 45 degrees Fahrenheit.

*Disases.*—No unusual susceptibility to diseases noted to date.

*Insects.*—Typical of this plant genius, white flies can be attracted to Lantana. There are no other insect problems known at this time.

GENERAL OBSERVATIONS

*Lantana camara* 'Robcomplan', with its dwarf and very compact growth habit is ideal for the smaller garden and landscape designs and the patio/pot culture trend. The lack of need to pinch for compact growth and the self-branching quality is a very time saving feature for the home gardener.

For the purpose of ornamental horticulture in our present living environments which include smaller yards and patio gardening, *Lantana camara* plant "Robcomplan" is ideal due to several characteristics:

A. It is an excellent plant for mass plantings, low borders, hanging baskets or floral specimen standards. *Lantana camara* 'Robcomplan' will produce a continuous display of bright, multiple colors in the hot summer sun when other color has disappeared.

B. Self-branching is spontaneous, so almost no pinching is necessary. This growth habit, atypical in lantanas, produces a full compact display plant with little care or attention on the part of the gardener.

C. The leaves are smaller and more closely arranged than other Lantanas, which enhances the "compacta" display. It forms a compact mound 12"×12" in one season. It's very compact growth habit with small leaf size, short internode spacing, and tendency toward self-branching places "Robcomplan" in a category all its own, as this "compact habit" is not typical for any other Lantana in our awareness.

D. *Lantana camara* 'Robcomplan' has a reduced tendency to set seed, therefore the inflorescence gives a longer display of color to the garden.

COMPARISON TO KNOWN VARIETIES

*Lantana camara* plant 'Robcomplan' is similar to *Lantana camara* Confetti' in color. The inflorescence form and color presentations of these two cultivars are similar. There are no Lantanas in the trade that are a close comparison to "Robcomplan" in reference to its very compact growth habit, short internode spacing, and strong tendency to self branching. For Example: In one growing season of four months, 'Confetti' forms a loose, open mound of 24"×24" with internode spacing of 1½"–2½". During this same growing period, 'Robcomplan'"forms a dense, compact mound of 12"×12" with internode spacing of ¾"–1".

I claim:

1. A new and distinct cultivar of Lantana plant, substantially as described and illustrated herein, characterized particularly as to novelty by its very compact growth habit with short internode spacing and strong tendency to self branching, with a continuous multi-colored bloom display, a reduced tendency to set seed, and dense, rich forest green leaves providing a cultivar well suite for mass plantings, low borders, hanging baskets or floral specimens having no unusual susceptibility to traditional Lantana diseases and insects.

* * * * *